US007860218B2

(12) United States Patent
Inglese et al.

(10) Patent No.: US 7,860,218 B2
(45) Date of Patent: Dec. 28, 2010

(54) METHOD FOR SERVOING A SOURCE OF X-RAYS OF A DIGITAL RADIOGRAPHY DEVICE

(75) Inventors: Jean-Marc Inglese, Bussy-Saint-Georges (FR); Sylvie Marie Gisèle Bothorel, Paris (FR); Alain Paul Lemaire, Quincy-Voisins (FR); Alain Boucly, Chauconin-Neufmontiers (FR)

(73) Assignee: Trophy, Croissy Beaubourg (FR)

( * ) Notice: Subject to any disclaimer, the term of this patent is extended or adjusted under 35 U.S.C. 154(b) by 0 days.

(21) Appl. No.: 12/093,456

(22) PCT Filed: Oct. 19, 2006

(86) PCT No.: PCT/EP2006/010060

§ 371 (c)(1),
(2), (4) Date: Sep. 23, 2008

(87) PCT Pub. No.: WO2007/057083

PCT Pub. Date: May 24, 2007

(65) Prior Publication Data

US 2009/0220044 A1    Sep. 3, 2009

(30) Foreign Application Priority Data

Nov. 15, 2005   (EP)   .................. 05356199

(51) Int. Cl.
*H05G 1/64* (2006.01)
(52) U.S. Cl. ........................................ 378/98.8
(58) Field of Classification Search .............. 378/62, 378/98.8, 114–116, 207
See application file for complete search history.

(56) References Cited

U.S. PATENT DOCUMENTS 6,307,915 B1 * 10/2001 Frojdh .................... 378/98.8

* cited by examiner

*Primary Examiner*—Courtney Thomas
(74) *Attorney, Agent, or Firm*—Young & Thompson

(57) ABSTRACT

The invention relates to a radiographic device and method of servoing an X-ray source (800) in a radiography device comprising a MOS-type image sensor (810) with pixels provided with separate read and refreshment commands, respectively, in which, during a radiography operation, read commands of a plurality of image sensor pixels are called repeatedly, while maintaining a source of X-rays power-supplied, so as to establish, in response to each reading, at least one image acquisition characteristic, and in which the emission of X-rays is interrupted when the image acquisition characteristic corresponds to a preset image acquisition characteristic.

11 Claims, 4 Drawing Sheets

METHOD FOR SERVOING A SOURCE OF X-RAYS OF A DIGITAL RADIOGRAPHY DEVICE

TECHNICAL FIELD

The present invention relates to a method for servoing a source of X-rays of a digital radiography device and digital radiography equipment using a servoed source. The invention has applications in the field of medical radiography, and in particular that of dental radiography.

STATE OF THE PRIOR ART

Digital radiography devices have a sensor capable of generating electrical signals that are a function of the radiation intensity, and more precisely the energy received at any point on a sensitive surface. Therefore, the sensor's sensitive surface is subdivided into a matrix of sensitive elements that, by analogy with the image capable of being formed based on the sensor's signal, are also called "pixels". The sensitive surface is linked to a scintillator that converts the X-rays received by the sensor into radiation whose wavelength is compatible with the pixels' sensitivity spectrum.

Two separate technologies are used to constitute the sensor's pixels. The first, known as CCD (Charge Coupled Device), operates according to a principle of charge accumulation, in response to the received radiation. During sequential reading, the charges are transferred cumulatively from one pixel to the next pixel of a row or column of pixels of the matrix. Charge transfer is synchronized by means of shift registers controlled by a clock. Charge transfer also causes refreshment of the pixels, which are fully discharged on reading.

A second technology is known as MOS (Metal Oxide Semi-conductor) or CMOS (Complementary Metal Oxide Semiconductor). This uses field-effect transistors with insulated gate. Each pixel has an internal capacity, charged (or discharged, respectively) during a refreshment step, and a photosensitive diode that, under the effect of radiation, gradually discharges (or charges, respectively) the capacity. On reading, the voltage is measured at the terminals of the capacity that decreases (or increases, respectively) in proportion to the quantity of radiation received during an integration period running from the last refreshment. CMOS-type pixels can have separate commands to cause their reading and refreshment. Thus, simple reading does not necessarily mean refreshment.

Although sequential reading is not required for CMOS type pixels, it is nevertheless retained in a number of devices, following the example of CCD pixels. The sequential reading has the advantage of supplying the reading signal by using a reduced number of electrical conductors and thus electrical connections. Fewer conductors and connectors has a special advantage for intraoral sensors, i.e. sensors specific to dental radiography.

The sequential reading and refreshment of CMOS pixels is illustrated, for example, by documents (1) to (4) which can be referred to, although they do not come from the field of radiography.

One of the difficulties, which exists whatever the type of sensor pixels, is to control the source of X-rays to prevent both pixel overexposure and underexposure. Control of the X-ray source is also important for preventing the X-rayed patient from receiving an energy dose higher than strictly necessary to produce an image.

Therefore, it is known to place near the sensor's sensitive surface one or several dose sensors whose function is to measure the radiation energy received and cause the cutting of the source when a predetermined dose is reached. However, dose sensors are incapable of reporting the status of all parts of the image, and do not prevent the existence of local over- or underexposed zones. Indeed, a dose sensor just has to be located by a particularly dense or particularly transparent part of X-rayed tissue in order not to correctly report the dose received by other tissues. Such is the case, for example, of a dose sensor located in the alignment of a dental amalgam and the X-ray source.

Inappropriate exposure in relation to the sensor's nominal exposure latitude causes either significant degradation of the signal-to-noise ratio, or pixel saturation, and impairs, in both cases, the quality of the radiographic image.

DESCRIPTION OF THE INVENTION

It is the object of the invention to propose a method of servoing an X-ray source and a radiography device not having the above-mentioned problems.

One object in particular is to exactly control the radiation dose received, while preventing local overexposures or underexposures of the resulting radiographic image.

Another object is to control the source to optimize the exposure for a certain tissue type.

Another object is to limit the radiation dose received by the patient without impairing the quality of the radiographic images.

To achieve these objects, the invention's aim is more precisely a method of servoing an X-ray source in a radiography device comprising a MOS-type image sensor with pixels provided with separate read and refreshment commands, respectively, in which, during a radiography operation, read commands of a plurality of image sensor pixels are called repeatedly, while maintaining an emission of X-rays, so as to establish, in response to each reading, at least one image acquisition characteristic, and in which the emission of X-rays is interrupted when the image acquisition characteristic corresponds to a preset image acquisition characteristic.

The servoing of the source, i.e. maintaining or interrupting the emission of X-rays, preferably takes place by maintaining or interrupting the power supply of the X-ray source. Other servoing methods, using a shutter, also enable the emission of the rays to be interrupted.

Thanks to the use of MOS-type pixels, i.e. MOS or CMOS pixels with insulated grid, and in particular pixels with separate read command, it is possible to establish and monitor the evolution of the image characteristic without disturbing pixel image integration. Indeed, refreshment is caused only when an image of sufficient quality is available, i.e. after the preset acquisition characteristic is reached.

The characteristic selected to interrupt X-ray emission is no longer linked to a dose sensor, or even to several dose sensors, but is established from reading the number of sensor pixels that would be sufficient to provide a readable image. In an optimal manner, the reading signal of all the sensor pixels can be used to establish the image characteristics. It is also possible to use the signal of a pixel subset distributed, preferably uniformly, on the sensor's sensitive surface. This means using a subsampled image to establish the image acquisition characteristic, or, in other words, to establish the acquisition characteristic for a subsampled image representing the image capable of being produced by the sensor.

Various image acquisition characteristics can be established and selected for servoing the source. They include, for example, a number of pixels, selected from among all the sensor's pixels, or a pixel subset, corresponding to at least one value of image density, i.e. whose signal is less than a preset value.

According to another option, the acquisition characteristic is a spreading of the pixel density spectrum. The preset characteristic is then a threshold spread value.

According to yet another option, the acquisition characteristic is a histogram. The histogram, capable of being represented graphically, is understood as a relationship between the densities, i.e. grey values of the image capable of being formed at a given time based on the read signal, and the number of image pixels respectively having these densities.

The preset characteristic selected is then a particular characteristic of all or part of the histogram. In particular, the preset characteristic can be a particular histogram shape or a histogram shape centered on at least one from among the peaks characteristic of soft tissue, bone and dentine, enamel and/or opaque material.

Opaque material means material such as amalgam or metal parts liable to be found in the patient's mouth.

When the acquisition characteristic corresponds to the preset characteristic, the sensor pixels are read to supply a useful read signal for image forming. As soon as the read signal is available, the pixel refreshment command can be called on.

The invention also relates to a radiography device comprising an X-ray source and a MOS-type image sensor with pixels provided with separate read and refreshment commands respectively, a sequencer to apply to the read commands a series of request signals, distributed over a radiation exposure period, and a computer. The computer receives the read signals supplied by the pixels in response to the request signals, to establish an image acquisition characteristic and to compare the acquisition characteristic with a preset acquisition characteristic. Finally, a means of interruption of the radiation exposure, controlled by the computer, is provided to interrupt the exposure when the image acquisition characteristic corresponds to the preset acquisition characteristic.

As previously indicated, the means to interrupt the exposure can act on the power supply of the X-ray source and/or on the propagation of the beam. This is, for example, a simple controlled switch connected in series in the electrical power supply circuit of the X-ray source.

The device can also comprise image reproduction means to produce an image from the read signals supplied by pixels. This is for example a computer or signal processing unit provided with a monitor or a printer, such as a laser printer.

Other characteristics and advantages of the invention will appear in the following description, which refers to the figures of the appended drawings. This description is given purely as an illustration and is not limiting.

DETAILED DESCRIPTION OF THE MODES OF IMPLEMENTING THE INVENTION

Figure 1:
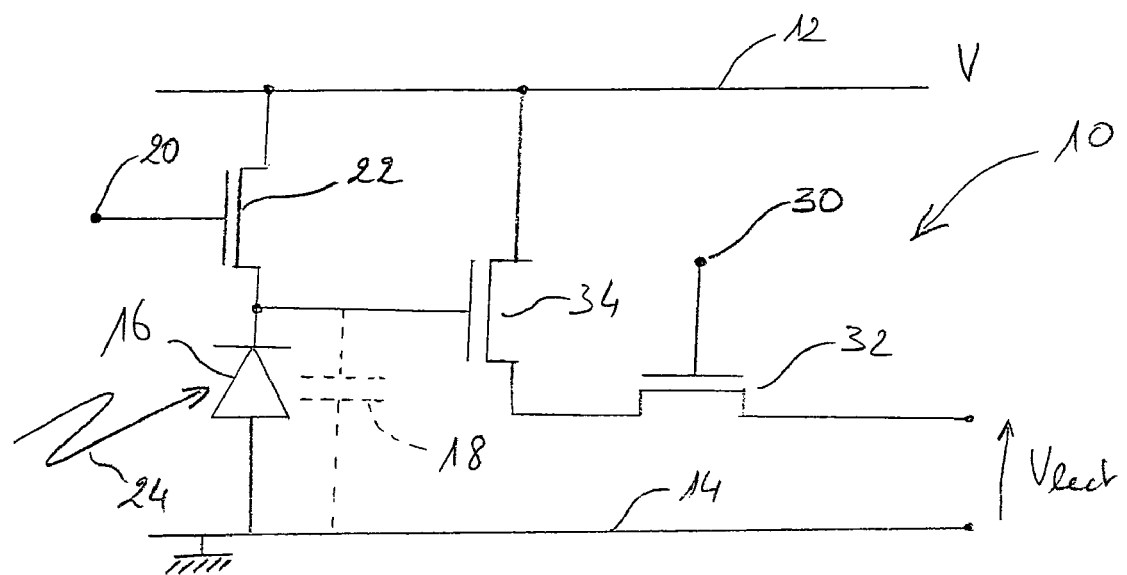
FIG. 1 is an electrical diagram of an individual CMOS type pixel with dual command capable of being used in a device according to the invention.

FIG. 1 shows an equivalent diagram of a MOS/CMOS type pixel 10 power supplied between a power supply line 12 and a reference line 14. The pixel is built around a light-sensitive diode 16 and a capacitor 18 connected in parallel to the diode. The capacitor is represented with a broken line, insofar as it is not a self-contained component but a capacity inherent to the MOS/CMOS structure.

Reference 20 indicates a terminal acting to command pixel refreshment. When a refreshment voltage is applied to the terminal 20, a transistor 22 connected to the power supply line 12 charges the capacitor 18, by raising its potential to a charge value V near the power supply voltage.

In the absence of light received by the pixel, the charge voltage V is conserved. However, in response to light radiation 24, an inverse current of the diode 16 gradually discharges the capacitor 18. The voltage at the terminals of the capacitor 18 thus decreases according to the light intensity received and according to the exposure duration. It should therefore be noted that the light radiation 24 received by the pixel is not X-rays but visible light radiation obtained by the conversion of the X-rays by a scintillator built into the image sensor.

Reference 30 indicates a terminal acting to command pixel reading. When an appropriate addressing pulse is applied to this terminal, a read transistor 32, associated with a follower transistor 34, delivers a read voltage $V_{read}$ representative of the residual charge voltage at the terminals of the capacitor 18. This read voltage can be used as the pixel read signal and be supplied by the sensor to an image display unit.

Thanks to the follower transistor 34, whose insulated grid is linked to the capacitor 18, the reading has no influence on the charge status of the capacitor 18, or on the voltage at its terminals. Thus the reading does not disturb the integration of the received light signal.

As an alternative, a pixel can be used that is more or less identical, but in which the diode's reverse current does not discharge but charges the capacitor. In this case, refreshment consists in discharging the capacitor and the received radiation tends to make the voltage increase at the capacitor's terminals. The following simple description is given for pixels whose voltage decreases with the received energy. It applies however, with the necessary changes having been carried out, for pixels corresponding to the variant given here.

Figure 2:
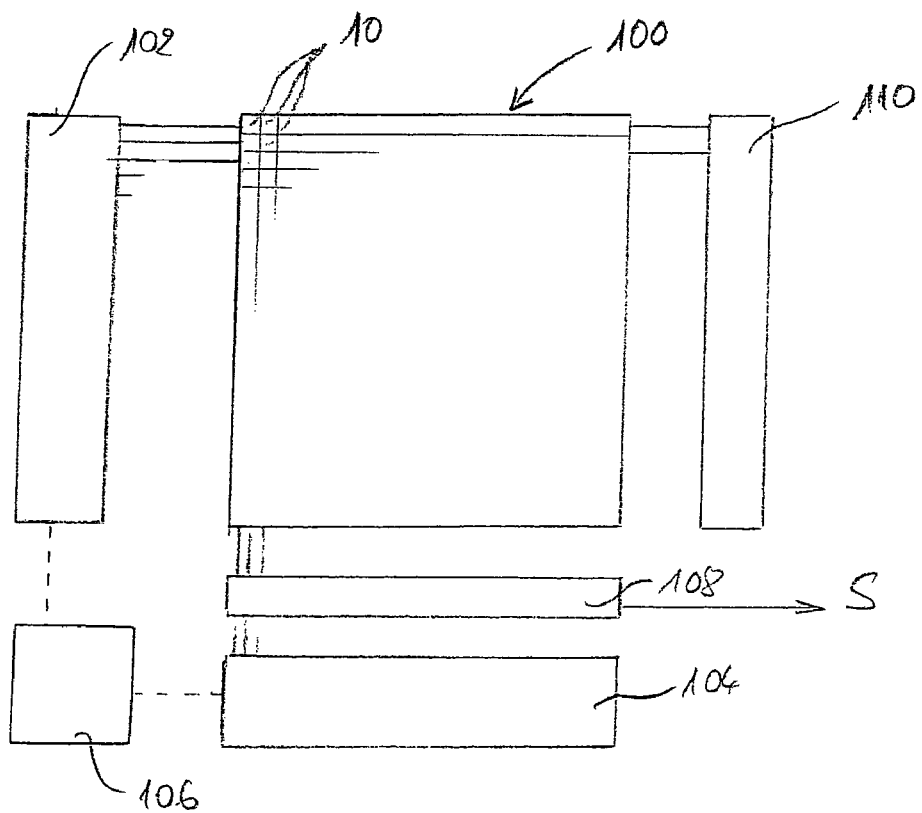
FIG. 2 is a schematic representation of a pixel matrix using pixels according to FIG. 1.

The pixel in FIG. 1 is integrated into a pixel matrix 100 of the image sensor. The pixels 10 are arranged in rows and columns, as shown in FIG. 2.

A read signal of the image sensor is obtained by sequentially addressing the sensor's pixels by means of row and column shift registers. The registers have references 102 and 104. They are synchronized by a clock or sequencer 106. Combined with column amplifiers 108, they deliver a sequential read signal S. Given that the components are MOS/CMOS, simultaneous in parallel reading of the pixels is also possible. However, sequential reading, comparable to reading CCD type pixels, has the special feature of enabling signal transfer using fewer electrical conductors. The signal can be transmitted, for example, on a two-wire cable. This aspect provides an advantage for intraoral sensors whose connection and hygiene requirements are often difficult to reconcile.

The row shift register 102 enables the supply of pulses which when applied to read commands enable pixel voltages to be read. A unit 110, possibly combined with the register 102, is planned to supply refreshment pulses to the terminals 20 of each pixel.

Figure 3:
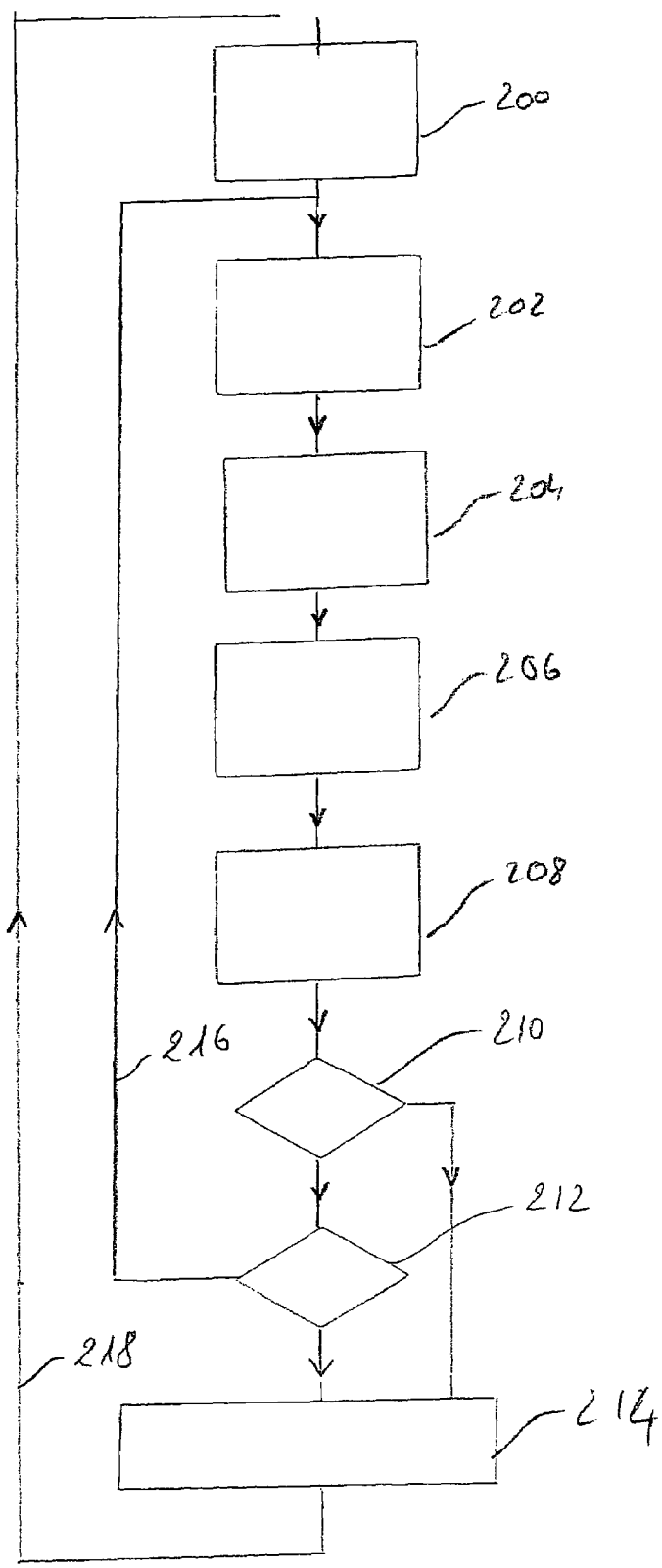
FIG. 3 is a flowchart describing a series of implementation steps of a method according to the invention.

An illustration of the operation of a device according to the invention is given by the flowchart of FIG. 3, together with the preceding description.

A first step 200 consists in refreshing all the sensor's pixels. Refreshment can be sequential or simultaneous for all the pixels or for a pixel subset. There follows an acquisition phase 202 in which an X-ray source of the radiography device is power supplied. The pixels integrate the light, and the voltage at the respective capacitor terminals decreases according to the received energy.

Acquisition is followed by a read step 204 in which a read signal is obtained by applying a read pulse to the command terminals of all the pixels or a pixel subset of the sensor. Preferably, this is a pixel subset capable of supplying an subsampled image.

Reading 204 is followed by a computing step 206 consisting in establishing an image acquisition characteristic, i.e. a characteristic that would be held by an image produced with the pixels at this stage of the acquisition. The acquisition characteristic is, for example, a histogram, or another of the above-mentioned characteristics.

As soon as the acquisition characteristic has been established, it is compared with a preset characteristic. This means, for example, comparing the number of pixels linked to a set of identical density values. When the acquisition characteristic is a histogram, the comparison can in particular relate to its spread width, envelope or surface area, or again the presence or location of characteristic peaks. It can also consist in a simple inter-correlation computation of a histogram and a preset histogram.

The result of the comparison 208 is the measurement of one or several values of difference between the acquisition characteristic and the preset characteristic.

The acquisition is continued during the read, computation and comparison steps. However, these steps are executed fast enough for the acquisition characteristics to be considered more or less unchanged.

The comparison step 208 is followed by two decision-making steps. A first decision-making step 210 consists in determining whether an overall exposure time is reached or not. If it is reached, the source's power supply is interrupted to prevent a dose of too high exposure for the patient, and the process is completed by generating an image based on the read signal of all or part of the sensor's pixels. The interruption of the exposure to X-rays and the production of an image based on the read signals available at this time is shown by reference 210 on FIG. 3. If the overall exposure time is not reached, a second decision-making step 212 takes place. It consists in either continuing, or interrupting the exposure. The exposure is continued if the difference between the acquisition characteristic and the preset characteristic is too large, i.e. if the preset characteristic is not reached. Otherwise, i.e. when the preset characteristic is reached or exceeded, the final step 214 is taken. In this case, X-ray emission is also interrupted and an image is formed with the pixel read signals.

If the exposure is continued, steps 202 to 212 are iterated as shown by an arrow 216.

The establishment of a radiographic image at step 214 can be followed, as shown by an arrow 218, by the refreshment of all the pixels ready for a new shot.

Figure 4:
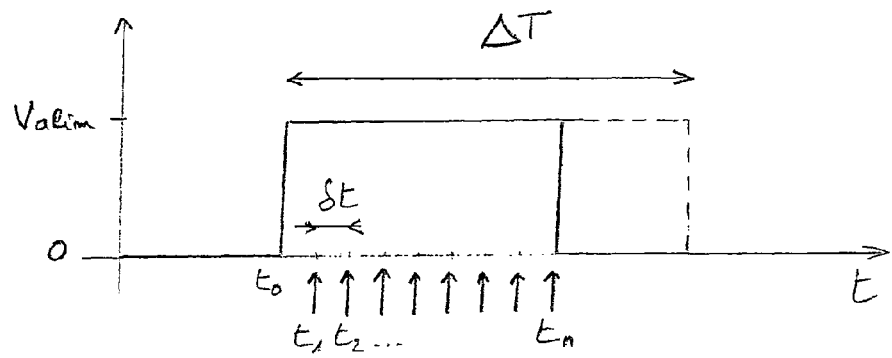
FIG. 4 is a simplified chronogram illustrating an operating aspect of a device according to the invention.

The chronogram in FIG. 4 best illustrates device operation over time. The chronogram shows as ordinate the power supply voltage applied to the X-ray source of the radiography device. It is assumed that the source only emits X-rays when the voltage equals the nominal power supply value $V_{ps}$. As abscissa, the chronogram shows time not to scale.

At a time $t_0$, the source is powered, and the sensor, whose pixels have previously been refreshed, integrates the received light. The maximum exposure duration, noted $\Delta T$, is set according to the maximum X-ray dose that is required to be administered to a patient. It is in the order of 80 to 200 milliseconds.

During this duration, at regular or irregular intervals $\delta t$, that are closer, i.e. of the order of 10 to 15 milliseconds, intermediate readings of all or part of the pixels are made by actuating the read commands as previously described. The intermediate readings are shown by small vertical arrows. They are used to assess whether the preset acquisition characteristic is reached or not. When this is the case, i.e. here at time $t_n$ shown in FIG. 4, the pixel read signal is used to establish a radiographic image and the X-ray source is shut down. Thus it can be seen that part of the exposure time has been reduced. This part is shown by broken line, for information.

Figure 5:
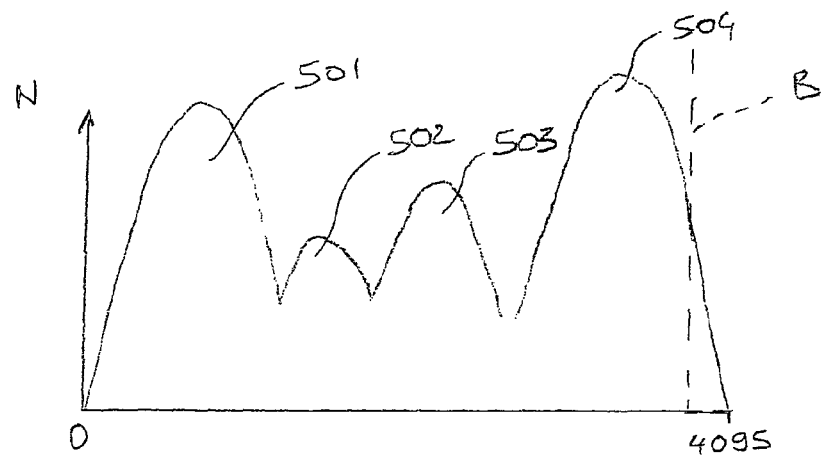
FIGS. 5 to 7 are histograms illustrating various stages of radiographic image acquisition.
Figure 6:
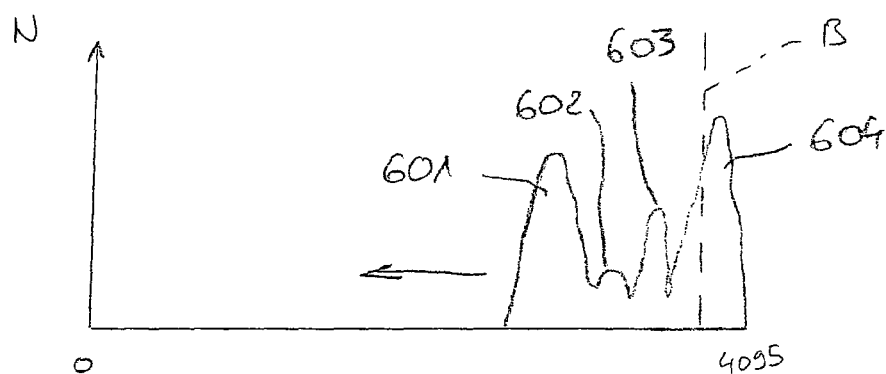
Figure 7:
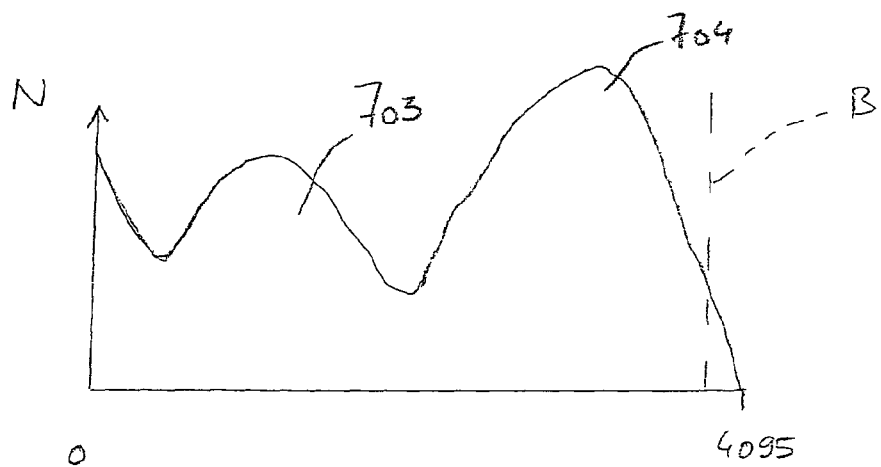

FIGS. 5, 6 and 7 illustrate the use of a particular image acquisition characteristic, in the form of histograms. This illustration is given for the particular case of the dental radiograph.

FIG. 5 shows a typical histogram of a correctly exposed dental radiograph, exactly covering the available exposure latitude. The histogram shows as abscissa a range of density values, or grey levels, which continuously extends from low densities (black) corresponding to transparent tissues, on the left-hand side of the figure, to the high densities (white) corresponding to opaque tissues, on the right-hand side of the figure. As ordinate, the histogram shows the number of pixels corresponding to each respective density value. As the sensor signal is digitized, coded in this case to 12 bits, the density values are spread out between 0 and 4095. A broken line B shows a limit above which the number of X-photons received is low and where the signal-to-noise ratio is degraded to the point of no longer distinguishing radiographed tissues.

The histogram in FIG. 5 shows four peaks that correspond to characteristic densities of a dental radiograph. A first low density peak 501 corresponds to the patient's cheek. A second denser peak 502 corresponds to the bone of the jaw or tooth dentine. A third yet denser peak 503 corresponds to the tooth enamel. Finally, a fourth almost opaque peak 504 corresponds to any amalgam present on a tooth. The envelope, or spread of a histogram comparable to that of FIG. 5 can be used, for example, as the preset acquisition characteristic.

For comparison, FIG. 6 shows a histogram established at the time of an intermediate reading of pixels. The received dose is still low and the histogram peaks 601, 602, 603, and 604 that correspond to the FIG. 5 peaks 501, 502, 503 and 504, respectively, are gathered at the high densities side, i.e. opaque materials. This is due to the low quantity of light integrated at this time. For example, this is time t1 of FIG. 4. As the exposure to X-rays continues, the histogram evolves, the peaks grow and the spread increases in the direction shown by an arrow to give the shape of FIG. 5. At this point, the exposure to X-rays can be suspended.

If the exposure continues, however, the histogram evolves further and takes a shape as shown in FIG. 7. Only the peaks 703 and 704, corresponding to peaks 503 and 504 of FIG. 1, respectively, remain. The other peaks have disappeared to the left-hand side of the histogram. This conveys over-exposure or blooming of the sensor, i.e. full discharge of the capacitor from an increasing number of its pixels.

Different preset acquisition characteristics can be taken according to the type of examination that the practitioner wishes to perform. The histogram of FIG. 5 can be taken as the preset histogram for overall examination of the mouth. The histogram of FIG. 6 can be taken for an examination limited to soft transparent tissues, while that of FIG. 7 can be taken as preset for an examination of the enamel or amalgams.

Figure 8:
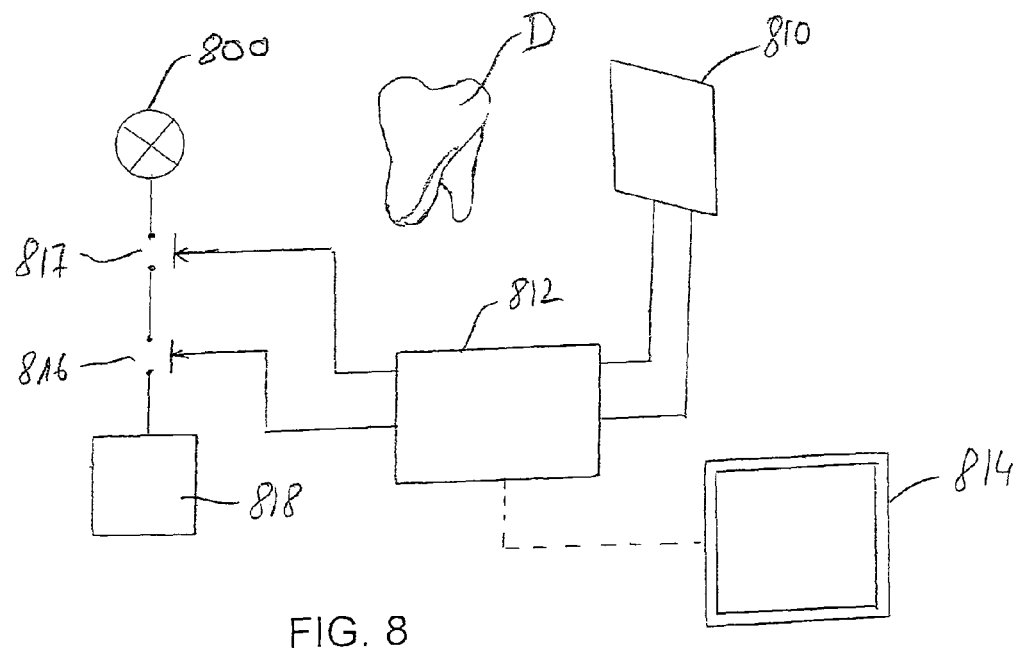
FIG. 8 is a simplified and schematic representation of a device according to the invention.

FIG. 8 shows in a simplified way a device implementing the described method. It comprises the X-ray source shown by reference 800, a CMOS-type sensor shown as reference 810, a computer 812, and a monitor 514. The computer 812, e.g. a PC, or a dedicated unit, has several functions. One of these functions is to collect the read signal of the pixels of the sensor 810 and to supply the sensor with read and refreshment pulses. For this purpose, it includes a sequencer. The computer 812 also establishes the image acquisition characteristics and compares them with a preset characteristic in the manner already described. It can also use read signals to format an image reproduced by a linked monitor or screen 814.

Finally, the computer controls two switches 816 and 817 connected in series in a power supply circuit linking an electrical power supply source 818 to the X-ray source. The first switch 817 is provided to interrupt X-ray transmission when a preset maximum duration ΔT is reached. The second switch is provided to interrupt the power supply when the preset acquisition value is reached.

Reference D symbolically represents tissues, in particular a tooth, located in the radiography field between the source and the sensor. The sensor 810 is in particular an intraoral sensor.

CITED DOCUMENTS

1) U.S. Pat. No. 6,856,249
2) U.S. Pat. No. 6,230,975
3) US 2002/0134911
4) EP-B-0858212

The invention claimed is:

1. A method of servoing an X-ray source (800) in a radiography device comprising:
    calling repeatedly during a radiography operation, read controls of a plurality of image sensor pixels provided via a MOS-type image sensor (810) with pixels (10) with separate read (30) and refreshment (20) controls, respectively;
    maintaining a source of X-rays power supplied, to establish, in response to each reading, at least one image acquisition characteristic; and
    interrupting the emission of X-rays upon the image acquisition characteristic corresponding to a preset image acquisition characteristic.

2. The method according to claim 1, wherein the image acquisition characteristic is a histogram.

3. The method according to claim 2, wherein the preset characteristic has histogram shape, and, in particular, a histogram shape centered on at least one from among the peaks (501, 502, 503, 504, 601, 602, 603, 604, 703, and 704) characteristic of soft tissue, bone and dentine, enamel and opaque materials.

4. The method according to claim 1, wherein the image acquisition characteristic is a number of pixels corresponding to at least one image density value.

5. The method according to claim 1, wherein the image acquisition characteristic is a spreading of the density spectrum exceeding a threshold value.

6. The method according to claim 1, wherein read controls are transmitted to all the pixels of the image sensor, respectively to a pixel subset of the image sensor, and the image acquisition characteristic is established based on the read signals of all the pixels, respectively, of the pixel subset of the image sensor.

7. The method according to claim 6, wherein the pixel subset comprises pixels uniformly distributed on the sensor surface.

8. The method according to claim 1, wherein the read controls are called in a sequential manner.

9. The method using the servoing method of claim 1, wherein the sensor pixels are read when the image acquisition characteristic corresponds to a preset image acquisition characteristic, and an image is formed based on a read signal obtained during the reading.

10. A radiography device comprising:
    an X-ray source (806) and a MOS-type image sensor (810) with pixels provided respectively with separate read and refreshment controls;
    a sequencer to apply to the read controls a series of call signals, distributed over a radiological exposure period;
    a computer (812) receiving the read signals supplied by the pixels in response to the call signals, to establish an image acquisition characteristic and to compare the acquisition characteristic with a preset acquisition characteristic; and
    means (817) of interrupting the radiological exposure, controlled by the computer, to interrupt the exposure when the acquisition characteristic corresponds to the preset image acquisition characteristic.

11. The device according to claim 10, also comprising image reproduction means (814) to supply an image based on the read signals supplied by the pixels.

* * * * *